United States Patent [19]

Binder et al.

[11] Patent Number: 4,818,760
[45] Date of Patent: Apr. 4, 1989

[54] DERIVATIVES OF PYRIDYLSULFINYL(BENZ-OR THIENO-)IMIDAZOLES AND THEIR USE AS GASTRIC SECRETION INHIBITING SUBSTANCES

[75] Inventors: Dieter Binder, Vienna; Franz Rovenszky, Bruck an der Leitha; Hubert P. Ferber, Ansfelden, all of Austria

[73] Assignee: Chemie Linz Aktiengesellschaft, Linz, Austria

[21] Appl. No.: 94,594

[22] Filed: Sep. 9, 1987

[30] Foreign Application Priority Data

Sep. 10, 1986 [AT] Austria .................................. 2437/86

[51] Int. Cl.$^4$ ..................... A61K 31/44; C07D 401/00
[52] U.S. Cl. ..................................... 514/338; 546/271
[58] Field of Search ....................... 546/271; 514/338

[56] References Cited

U.S. PATENT DOCUMENTS

| | | | |
|---|---|---|---|
| 4,045,564 | 8/1977 | Berntsson et al. | 546/271 |
| 4,255,431 | 3/1981 | Junggren et al. | 546/271 |
| 4,337,257 | 6/1982 | Junggren et al. | 546/271 |
| 4,508,905 | 4/1985 | Junggren et al. | 546/271 |
| 4,621,084 | 11/1986 | Takaya et al. | 546/271 |

FOREIGN PATENT DOCUMENTS 0173664  3/1986  European Pat. Off. ............ 546/271

*Primary Examiner*—Alan L. Rotman
*Assistant Examiner*—Robert C. Whittenbaugh
*Attorney, Agent, or Firm*—Wenderoth, Lind & Ponack

[57] ABSTRACT

The invention relates to novel derivatives of 4,5-dihydrooxazoles of the formula

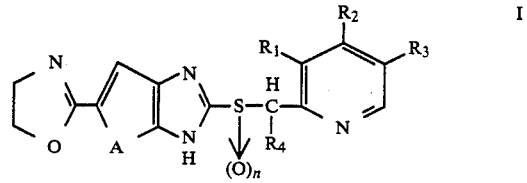

in which
  A denotes —CH=CH— or —S—,
  $R_1$, $R_3$ and $R_4$, independently of one another, denote hydrogen or lower alkyl,
  $R_2$ denotes hydrogen or lower alkoxy, and
  n denotes 0 or 1, a process for their preparation, and pharmaceutical preparations which contain these compounds. The novel compounds cause blockage of $H^+/K^+$ ATPase and can be used as active ingredients in medicaments for treatment and prophylaxis of disorders which are caused by increased gastric secretions.

6 Claims, No Drawings

DERIVATIVES OF PYRIDYLSULFINYL(BENZ-OR THIENO-)IMIDAZOLES AND THEIR USE AS GASTRIC SECRETION INHIBITING SUBSTANCES

Novel derivatives of 4,5-dihydrooxazoles, a process for their preparation, and their use

DESCRIPTION

The invention relates to novel derivatives of 4,5-dihydrooxazoles, a process for their preparation, and their use.

Substituted pyridylsulfinylbenzimidazoles and pyridylsulfinylthienoimidazoles having an inhibitory action on gastric secretions are known and described, for example in U.S. Pat. Nos. 4,255,431, 4,337,257, 4,508,905 and EP-A No. 201,094. However, since the pharmacological profile of action of these substances has not yet been fully tested, and it is thus not clear whether the substances can also be used effectively in human therapy, there continues to be a demand for novel compounds having a gastric secretion-inhibiting action.

Accordingly, the invention relates to novel 4,5-dihydrooxazoles of the formula

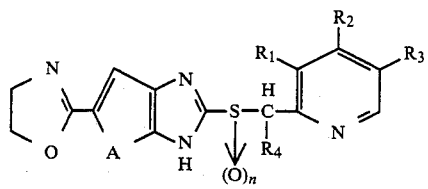

in which

A denotes —CH=CH— or —S—, $R_1$, $R_3$ and $R_4$, independently of one another, denote hydrogen or lower alkyl, $R_2$ denotes hydrogen or lower alkoxy, and n denotes 0 or 1, a process for their preparation, pharmaceutical preparations which contain these compounds, and their use.

The term "lower alkyl" used in this description denotes straight-chain or branched, saturated hydrocarbon groups having 1-4 carbon atoms, such as, for example, methyl, ethyl, propyl, isopropyl, butyl and tert.butyl. The term "lower alkoxy" relates to hydrocarboxy groups having 1-4 carbon atoms, for example methoxy, ethoxy, propoxy, isopropoxy, butyoxy and tert.butoxy.

In a preferred group of compounds of the formula I, $R_1$, $R_3$ and $R_4$ denote hydrogen or methyl and $R_2$ denotes hydrogen or methoxy.

A further preferred group within the compounds of the general formula I is that in which n denotes the number 1.

The compounds of the formula I can be prepared according to the invention in a process in which (a) a compound of the formula

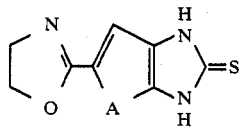

in which A has the meaning given in formula I, is reacted with a compound of the formula

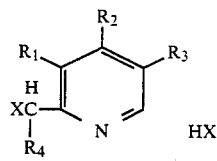

in which X represents chlorine or bromine and $R_1$, $R_2$, $R_3$ and $R_4$ have the meaning given in formula I, in the presence of at least 2 equivalents of a strong base, after which (b) the compounds thus obtained of the formula I in which n denotes 0 are reacted, if appropriate, with equivalent amounts of an organic peracid or hydrogen peroxide to form a compound of the general formula I in which n denotes the number 1.

The reaction in accordance with process step (a) is advantageously carried out by suspending the compounds of the formula II or III in an inert organic solvent, for example in a low-boiling aliphatic alcohol, such as methanol, ethanol, isopropanol and the like, preferably in methanol, the compounds of the formula II expediently being employed in excess for reasons of better work-up, and then at least 2 equivalents of a strong base, for example an alkali metal hydroxide or alkali metal carbonate, preferably NaOH or KOH, dissolved in a little water are added dropwise at room temperature. If the reaction is performed without any water, an alkali metal hydride or alkali metal alcoholate can be used as the strong base and DMF or a water-free alcohol can be used as an inert organic solvent.

Depending on the starting compounds, the solvent and the temperature, the reaction time is about 2-8 hours.

According to process step (b), the sulfoxide compounds in which n denotes the number 1 in formula I can be obtained starting from the sulfide compounds where n=0 obtained according to process (a) by partial oxidation using suitable oxidants. The oxidants used are preferably approximately equivalent amounts of an organic peracid, such as peracetic acid, perbenzoic acid or m-chlorobenzoic acid, in an inert solvent, for example methylene chloride or chloroform, at temperatures between about −10° C. and −50° C., or approximately equivalent amounts of 30 percent strength $H_2O_2$ in glacial acetic acid at room temperture.

The compounds of formula I are subject to tautomerism and can thus also exist in all the tautomeric forms of the formula I.

The starting compounds of the general formula III are known. The starting compounds of the general formula II used for the process can be prepared in a fashion which is known per se starting from known products. In particular, they can be synthesized according to the following reaction equation and according to the specific instructions in the examples. The starting compounds of the formulae IV (Fluka Article No. 25450) and IX (C. D. Hurd and K. L. Kreuz, J. Am. Chem. Soc. 74, 2965 (1952) specified in the reaction equation are known from the literature.

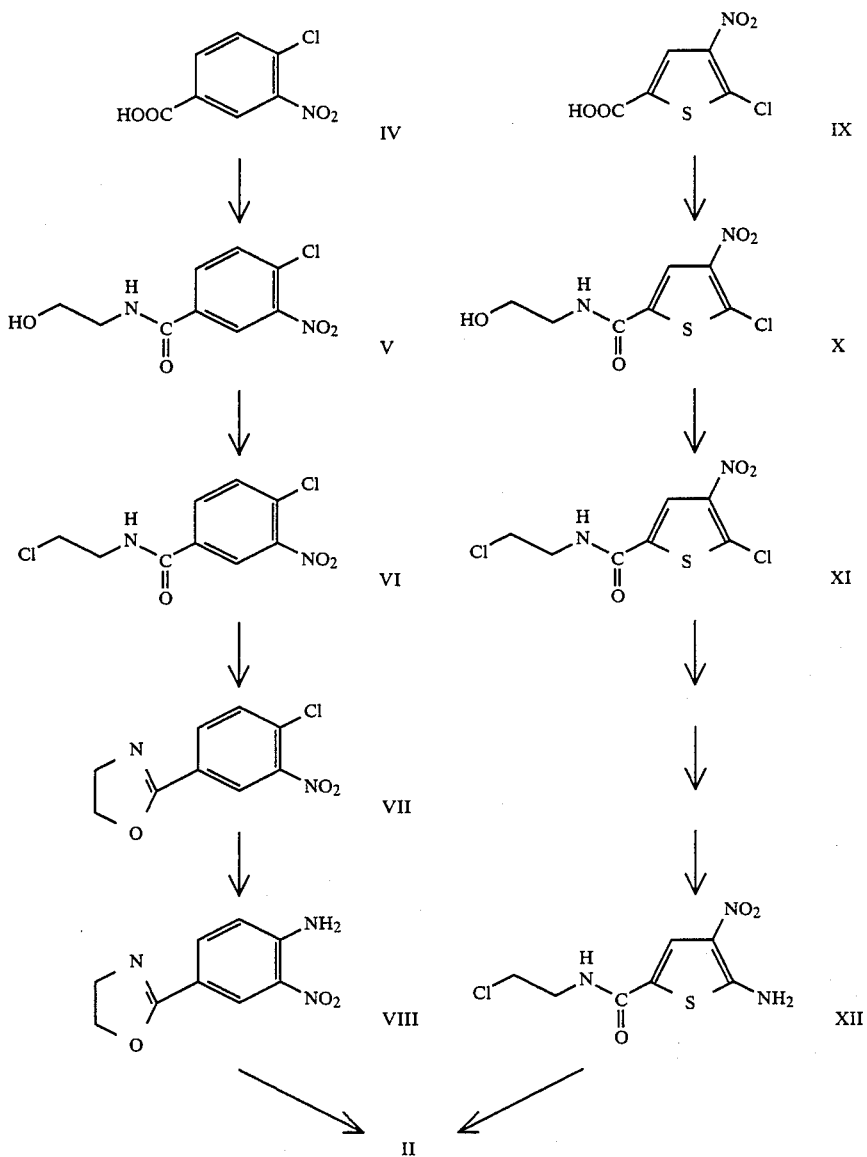

The compounds of formula I have valuable pharmacological properties. In particular, they cause blockage of $(H^+ + K^+)$-ATPase and can thus be employed, for example, in human medicine for treatment or prophylaxis of gastric and duodenal ulcers and other disorders caused by increased gastric secretions. In the enzyme test, they have proven approximately five times as effective as omeprazole, the preferred substance of EP No. 5129.

The compounds of formula I can also be used in other mammals besides humans.

The daily dose in man depends on the compound used, as well as on other factors, such as severity of the disease, how the compound is administered or on the type of formulation. In the case of oral administration, in a man of normal weight, the daily dose is approximately between 0.2 and 100 mg/kg body weight, preferrably between 0.5 and 5 mg/kg body weight, but it may also be above or below these ranges, depending on the doctor's orders.

The compounds of formula I can be used as medicines, for example in the form of pharmaceutical preparations, which contain the compounds according to the invention mixed with a pharmaceutical, organic or inorganic excipient which is suitable for enteral or parenteral administration, for example water, gelatin, gum arabic, lactose, starch, magnesium stearate, talc, vegetable oils, polyalkylene glycols, vaseline or the like. The pharmaceutical preparations can exist in solid form, for example as tablets, coated tablets, suppositories, or capsules, or in liquid form, for example as solutions, suspensions or emulsions. If appropriate, they are sterilized and/or control adjuvants, such as preservatives, stabilizers or emulsifiers, salts for modifying the osmotic pressure, or buffers. They can also be administered together with other therapeutically valuable substances.

EXAMPLE 1

5-(4,5-dihydro-2-oxazolyl)-2-((3,5-dimethyl-4-methoxy-2-pyridyl)-methylthio)-1H-benzimidazole
(Formula I: A=CH=CH, $R_1$ and $R_3$=CH$_3$, $R_2$=OCH$_3$, $R_4$=H, and n=0)

6.00 g (27.4 mmol) of 5-(4,5-dihydro-2-oxazolyl)-1,3-dihydrobenzimidazole-2-thione (formula II: A=CH=CH) and 6.08 g (27.4 mmol) of 2-chloromethyl-4-methoxy-3,5-dimethylpyridine hydrochloride are suspended in 120 ml of methanol, and 27.8 ml (55.6 mmol) of 2N aqueous NaOH are added dropwise within 12 minutes. During this addition, the temperature increases to 30° C. The mixture is stirred at room temperature for a further 3 hours and evaporated to dryness, and the residue is taken up in 140 ml of water. The mixture is acidified to pH 4.5 by adding glacial acetic acid and extracted three times with 200 ml of chloroform in each case. The combined organic phases are dried over sodium sulfate/activated charcoal, filtered and evaporated. The residue is digested with acetonitrile, and the crystals are filtered off under suction and dried at 50° C./20 mbar.

For further purification, the product is recrystallized from acetone.

Yield: 5.6 g of yellowish crystals (55.5% of theory)
Melting point=188°–90° C. (acetone)
The starting material can be prepared as follows:
4-chloro-N-(2-hydroxyethyl)-3-nitrobenzamide (V)
64.4 g (0.319 mol) of 4-chloro-3-nitrobenzoic acid are stirred into 400 ml of thionyl chloride, and the mixture is refluxed for 3 hours. The mixture is subsequently evaporated, and the residue is dissolved in 300 ml of absolute methylene chloride. This solution is added dropwise within 2 hours to a solution of 40.9 g (0.670 mol) of ethanolamine in 400 ml of absolute methylene chloride at −10° C. The mixture is stirred for a further 30 minutes, and the precipitate is filtered off under suction, washed twice with 100 ml of 0.25N HCl in each case and once with 100 ml of water and dried at 50° C./20 mbar.

Yield: 83.1 g of pale yellow crude product, containing 1 mol of water of crystallization (99% of theory)
Melting point=130°–3° C. (dioxane)
4-chloro-N-(2-chloroethyl)-3-nitrobenzamide (VI)
101.0 g (0.385 mol) of 4-chloro-N-(2-hydroxyethyl)-3-nitrobenzamide.H$_2$O are stirred in portions into 450 ml of thionyl chloride. The mixture is stirred at room temperature for a further 30 minutes and subsequently evaporated in vacuo.

Yield: 99.1 g of yellowish crystals (98% of theory)
Melting point=94°–6° C. (dioxane)
2-(4-chloro-3-nitrophenyl)-4,5-dihydrooxazole (VII)
99.0 g (0.376 mol) of 4-chloro-N-(2-chloroethyl)-3-nitrobenzamide are heated to 70° C. with stirring in 800 ml of ethanol, and 217 ml (0.434 mol) of 2N aqueous NaOH are added. The mixture is stirred at 70° C. for a further 30 minutes and then evaporated, and the residue is taken up in water. The solid product is filtered off under suction, washed with water and dried at 50° C./20 mbar.

Yield: 74.2 g (87% of theory)
Melting point=89°–90° C. (diisopropyl ether)
2-(4-amino-3-nitrophenyl)-4,5-dihydrooxazole (VIII)
10.0 g (44.1 mmol) of 2-(4-chloro-3-nitrophenyl)-4,5-dihydrooxazole are heated for 9 hours at 125° C. in a steel autoclave in 60 ml of tert.-butylamine. The mixture is subsequently evaporated in vacuo, and the dry, finely powdered residue is stirred at 80° C. in 20 ml of 85 percent strength o-phosphoric acid. The mixture is stirred at 80° C. for 30 minutes, subsequently cooled, emptied into 125 ml of ice water, covered with 15 ml of ethyl acetate, adjusted to pH 8 using ammonia with ice cooling and stirred vigorously for 10 minutes, and the deposited precipitate is filtered off under suction. It is washed with water and a little ethyl acetate and dried at 50° C./20 mbar.

Yield: 5.7 g of yellow crystals (62.3% of theory)
Melting point=215°–7° C. (methanol)
5-(4,5-dihydro-2-oxazolyl)-benzimidazole-2-thione (II: A=CH=CH)
10.0 g (48.3 mmol) of 2-(4-amino-3-nitrophenyl)-4,5-dihydroxyooxazole are dissolved in 80 ml of dioxane and 400 ml of methanol and hydrogenated at room temperature in a medium-pressure hydrogenation apparatus using W$_2$ Raney nickel until the calculated amount of hydrogen has been taken up. The catalyst is filtered off under suction through a filtration aid, and the filtrate is evaporated to dryness. The residue is dissolved in 500 ml of ethanol, 9.4 g (72.2 mmol) of sodium methylxanthogenate are added, and the mixture is refluxed for 3 hours. The mixture is then evaporated in vacuo, and the residue is taken up in 200 ml of water and dissolved by adding 13 ml of 2N NaOH. 2 spoons of activated charcoal are added, and the mixture is stirred briefly and filtered off under suction through a filtration aid. The filtrate is acidified to pH 4.5 using glacial acetic acid, and the deposited precipitate is filtered off under suction and washed three times with water. It is dried at 60° C./20 mbar.

Yield: 7.4 g of brownish crystals (69.9% of theory)
Melting point=265°–8° C. (partial decomposition from 200° C.)

EXAMPLE 2

5-(4,5-dihydro-2-oxazolyl)-2-((4-methoxy-2-pyridyl)-methylthio)-1H-benzimidazole (Formula I: A=CH=CH, R$_1$, R$_3$ and R$_4$=H, R$_2$=OCH$_3$ and n=0)
6.49 g (29.6 mmol) of 5-(4,5-dihydro-2-oxazolyl)-benzimidazole-2-thione (formula II: A=CH=CH) and 5.46 g (29.1 mmol) of 2-chloromethyl-4-methoxypyridine hydrochloride are suspended in 80 ml of methanol, and 30 ml (60 mmol) of 2N aqueous NaOH are added dropwise within 12 minutes. During this addition, the temperature increases to 30° C. The mixture is stirred at room temperature for a further 6 hours and evaporated to dryness, and the residue is taken up in 120 ml of water. The mixture is acidified to pH 4.5 by adding glacial acetic acid and is extracted three times with 200 ml of chloroform in each case. The combined organic phases are dried over sodium sulfate/activated charcoal, filtered and evaporated. The residue is crystallized from acetonitrile, the crystals are filtered off under suction and dried at 50° C./20 mbar. For further purification, the product is recrystallized from acetone.

Yield: 5.60 g of yellowish crystals (58.5% of theory)
Melting point=147°–9° C. (acetone)

EXAMPLE 3

5-(4,5-dihydro-2-oxazolyl)-2-((2-pyridyl)methylthio)-1H-benzimidazole (Formula I: A=CH=CH, R$_1$, R$_2$, R$_3$ and R$_4$=H and n=0)
6.00 g (27.4 mmol) of 5-(4,5-dihydro-2-oxazolyl)-1,3-dihydrobenzimidazole-2-thione (formula II: A=CH=CH) and 4.49 g (27.4 mmol) of 2-chloromethylpyridine hydrochloride are suspended in 120 ml of methanol, and 27.5 ml (54.7 mmol) of 2N aqueous KOH are added dropwise within 10 minutes, the temperature increasing to 28° C. The mixture is stirred at room temperature for 8 hours, the solvent is then removed by distillation, and the residue is taken up in 120 ml of water. The solution is acidified to pH=4.5 using glacial acetic acid and extracted by shaking three times with a total of 350 ml of methylene chloride. The combined organic phases are dried over sodium sulfate/activated charcoal, filtered and evaporated. The dark brown oil remaining is crystallized using acetonitrile, and the crystallization is completed overnight in a freezer. The crystals are filtered off under suction, washed with a little cold acetonitrile and dried at 50° C./20 mbar.

Yield: 5.70 g of beige crystals (67.1% of theory)
Melting point=178°-81° C. (acetone)

EXAMPLE 4

5-(4,5-dihydro-2-oxazolyl)-2-((3,5-dimethyl-4-methoxy-2-pyridyl)methylsulfinyl)-1H-benzimidazole (Formula I: A=CH=CH, $R_1$ and $R_3$=$CH_3$, $R_2$=$OCH_3$, $R_4$=H and n=1)

A solution of 3.65 g (18.0 mmol) of 85 percent strength 3-chloroperbenzoic acid in 65 ml of chloroform is added dropwise within 30 minutes to a solution of 6.5 g (17.6 mmol) of 5-(4,5-dihydro-2-oxazolyl)-2((3,5-dimethyl-4-methoxy-2-pyridyl)methylthio)-1H-benzimidazole in 200 ml of chloroform with stirring at a temperature between −12° and −10° C. The mixture is stirred at −10° C. for a further 1 hour and subsequently extracted twice with 40 ml of saturated sodium hydrogen carbonate solution. The aqueous phases are washed once with 50 ml of chloroform, and the combined organic phases are dried over sodium sulfate with addition of activated charcoal, filtered and evaporated. The residue is crystallized using ethanol and recrystallized from ethanol with addition of activated charcoal.

Yield: 3.05 g of yellowish crystals (45.0% of theory)
Melting point=112°-4° C., decomp. (ethanol)

EXAMPLE 5

5-(4,5-dihydro-2-oxazolyl)-2-((3,5-dimethyl-4-methoxy-2-pyridyl)-methylthio)-3H-thieno[2,3-d]imidazole (Formula I: A=S, $R_1$ and $R_3$=$CH_3$, $R_2$=$OCH_3$, $R_4$=H and n=0)

5.00 g (22.2 mmol) of 5-(4,5-dihydro-2-oxazolyl)-1,3-dihydrothieno[2,3-d]imidazole-2-thione (formula II: A=S) and 3.45 g (15.5 mmol) of 2-chloromethyl-4-methoxy-3,5-dimethylpyridine hydrochloride are suspended in 70 ml of methanol, and 20 ml (40 mmol) of 2N aqueous NaOH are added dropwise within 10 minutes. During this addition, the temperature increases to 32° C. The mixture is stirred at room temperature for a further 3 hours and evaporated to dryness, and the residue is taken up in 100 ml of water and 2 ml of glacial acetic acid. The solution is extracted three times with 70 ml of chloroform in each case. The combined organic phases are dried over sodium sulfate/activated charcoal, filtered and evaporated. The residue is digested using acetonitrile and the crystals are filtered off under suction and dried at 50° C./20 mbar.

For further purification, the product is again recrystallized from acetonitrile.

Yield: 4.56 g of yellowish crystals (78.4% of theory)
Melting point=decomp. from 191° C. (acetonitrile)

The starting material can be prepared as follows:
5-chloro-N-(2-hydroxyethyl)-4-nitro-2-thiophene-carboxamide (X)

36.9 g (0.178 mol) of 5-chloro-4-nitro-2-thiophene-carboxylic acid are stirred into 190 ml of thionyl chloride, and the mixture is refluxed for 3 hours.

Excess thionyl chloride is subsequently removed by distillation in vacuo. The residue is dissolved in 300 ml of absolute methylene chloride, and this solution is added dropwise at −15° C. to a solution of 23.2 g (0.380 mol) of ethanolamine in 120 ml of absolute methylene chloride within 2 hours. The mixture is stirred for a further 1 hour, and the deposited precipitate is filtered off under suction, washed once with 100 ml of 0.25N HCl and once with 100 ml of water, and dried at 40° C./20 mbar.

Yield: 35.7 g of pale yellow crystals (80.1% of theory)
Melting point=136°-8° C. (dioxane)
5-chloro-N-(2-chloroethyl)-4-nitro-2-thiophene-carboxamide (XI)

35.5 g (0.142 mol) of 5-chloro-N-(2-hydroxyethyl)-4-nitro-2-thiophenecarboxamide are stirred in portions into 180 ml of thionyl chloride at room temperature. After stirring at room temperature for 90 minutes, the mixture is evaporated in vacuo and dried at 40° C./20 mbar.

Yield: 37.5 g of pale yellow crystals (98.4% of theory)
Melting point=111°-4° C. (benzene)
5-amino-N-(2-chloroethyl)-4-nitro-2-thiophene-carboxamide (XII)

Ammonia gas is passed into a solution of 30.0 g (0.111 mol) of 5-chloro-N-(2-chloroethyl)-4-nitro-2-thiophenecarboxamide in 300 ml of absolute dioxane with stirring. When the initially exothermic reaction has subsided, the reaction mixture is stirred for a further 9 hours with continued passing-in of gas and subsequently evaporated in vacuo. The residue is distributed between water and ethyl acetate, and the phases are separated. The aqueous phase is extracted a further five times with 100 ml of ethyl acetate in each case, and the combined organic phases are dried over sodium sulfate with addition of activated charcoal, filtered and evaporated.

Yield: 25.7 g of yellow crystals (92.3% of theory)
Melting point=202°-8° C. (acetonitrile)
5-(4,5-dihydro-2-oxazolyl)-1,3-dihydrothieno[2,3-d]imidazole-2-thione (II: A=S)

10.0 g (40.1 mmol) of 5-amino-N-(2-chloroethyl)-4-nitro-2-thiophenecarboxamide are dissolved in 100 ml of dioxane and 100 ml of methanol and hydrogenated at room temperature in a medium-pressure hydrogenation apparatus using $W_2$ Raney nickel as catalyst until the calculated amount of hydrogen has been taken up. The catalyst is filtered off under suction through a filtration aid, and 6.3 g (48.0 mmol) of sodium methylxanthanogenate are added, and the mixture is refluxed for 2.5 hours. The reaction mixture is then evaporated, and the residue is taken up in 200 ml of water and 10 ml of saturated sodium carbonate solution. A small amount of insoluble residue is filtered off, the filtrate is acidified to pH 4.5 using glacial acetic acid, and the deposited precipitate is filtered off under suction, washed three times with water and dried at 60° C./20 mbar.

Yield: 3.3 g of greenish crystals (36.4% of theory)
Melting point >300° C. (partial decomp.)

EXAMPLE 6

5-(4,5-dihydro-2-oxazolyl)-2-((4-methoxy-2-pyridyl)-methylthio)-3H-thieno[2,3-d]imidazole (Formula I: A=S, $R_1$, $R_3$ and $R_4$=H, $R_2$=$OCH_3$ and n=0)

2.70 g (12.0 mmol) of 5-(4,5-dihydro-2-oxazolyl)-1,3-dihydrothieno[2,3-d]imidazole-2-thione (formula II: A=S) and 2.09 g (10.8 mmol) of 2-chloromethyl-4-methoxypyridine hydrochloride are suspended in 40 ml of methanol, and 13 ml (26.0 mmol) of 2N aqueous KOH are added dropwise within 15 minutes, the temperature increasing to 28° C. The mixture is stirred at room temperature for a further 7 hours and evaporated to dryness, and the residue is taken up in 50 ml of water and acidified to pH=4.5 using glacial acetic acid. The mixture is extracted three times with a total of 150 ml of chloroform. The combined organic phases are dried over sodium sulfate/activated charcoal, filtered and evaporated. The residue is digested using acetonitrile, and the crystals are filtered off under suction and dried at 50° C./20 mbar.

For further purification, the product is again recrystallized from acetonitrile.

Yield: 2.33 g of yellowish crystals (62.4% of theory)
Melting point=decomp. from 182° C. (acetinitrile)

EXAMPLE 7

5-(4,5-dihydro-2-oxazolyl)-2-((2-pyridyl)methylthio)-3H-thieno-[2,3-d]imidazole (Formula I: A=S, $R_1$, $R_2$, $R_3$ and $R_4$=H and n=0)

1.50 g (6.66 mmol) of 5-(4,5-dihydro-2-oxazolyl)-1,3-dihydrothieno[2,3-d]imidazole-2-thione (formula II: A=S) and 0.76 g (4.63 mmol) of 2-chloromethylpyridine hydrochloride are suspended in 30 ml of methanol, and 7 ml (14 mmol) of 2N aqueous NaOH are added dropwise within 15 minutes. During this addition, the temperature increases to 31° C. After stirring at room temperature for 2 hours, the mixture is evaporated, and the residue is taken up in 60 ml of water and 1.5 ml of glacial acetic acid and extracted three times with 50 ml of methylene chloride in each case. The combined organic phases are dried over sodium sulphate/activated charcoal, filtered and evaporated. The residue is digested using acetonitrile, and the crystals are filtered off under suction and dried at 50° C./20 mbar.

For further purification, the product is again recrystallized from acetonitrile.

Yield: 1.28 g of yellowish crystals (87.3% of theory)
Melting point=decomp. from 168° C. (acetonitrile)

EXAMPLE 8

5-(4,5-dihydro-2-oxazolyl)-2-((3,5-dimethyl-4-methoxy-2-pyridyl)-methylsulfinyl)-3H-thieno[2,3-d]imidazole (Formula I: A=S, $R_1$ and $R_3$=$CH_3$, $R_2$=$OCH_3$, $R_4$=H and n=1)

A solution of 1.63 g (8.01 mmol) of 85 percent strength 3-chloroperbenzoic acid of chloroform is added dropwise within 30 minutes to a solution of 3.0 g (8.01 mmol) of 5-(4,5-dihydro-2-oxazolyl)-2-((3,5-dimethyl-4-methoxy-2-pyridyl)methylthio)-3H-thieno[2,3-d]imidazole in 100 ml of chloroform with stirring at a temperature between −25° and −20° C. The mixture is stirred at −20° C. for a further 1 hour and subsequently extracted twice with 20 ml of saturated sodium hydrogen carbonate solution. The aqueous phases are washed once with 50 ml of chloroform, and the combined organic phases are dried over sodium sulfate with addition of activated charcoal, filtered and evaporated. The residue is crystallized using acetonitrile and recrystallized from ethanol with addition of activated charcoal.

Yield: 2.80 g of yellowish crystals (89.5% of theory)
Melting point=decomp. from 131° C.

EXAMPLE 9

5-(4,5-dihydro-2-oxazolyl)-2-((2-pyridyl)methylsulfinyl)-3H-thieno[2,3-d]imidazole (Formula I: A=S, $R_1$, $R_2$, $R_3$ and $R_4$=H, and n=1)

1.00 g (3.16 mmol) of 5-(4,5-dihydro-2-oxazolyl)-2-((2-pyridyl)methylthio)-3H-thieno[2,3-d]imidazole are taken up in 15 ml of glacial acetic acid, and 0.36 g (3.16 mmol) of 30 percent strength $H_2O_2$ is added dropwise at 5°–10° C. The mixture is stirred at room temperature for a further 30 minutes, diluted with 100 ml of water and extracted three times with 30 ml of methylene chloride in each case. The combined organic phases are washed with sodium hydrogen carbonate solution, dried over sodium sulphate, filtered and evaporated.

Yield: 0.64 g of yellowish crystals (60.9% of theory)
Melting point=decomp. from 190° C.

EXAMPLE 10

In a comparison experiment, the inhibitory action of omeprazole (the preferred compound of EP 5129) and the compound of Example 4 of the present application (substance A) on $H^+/K^+$-ATPase is investigated and the $IC_{50}$ calculated. In this experiment, the following values were found:

| | Inhibition of $H^+/K^+$-ATPase $IC_{50}$ ($\mu$mol) |
|---|---|
| Omeprazole | 28.0 |
| Substance A | 5.3 |

This comparison shows that substrate A inhibits $H^+/K^+$-ATPase approximately five times greater than does omeprazole.

What we claim is:

1. A 4,5-Dihydrooxazole of the formula

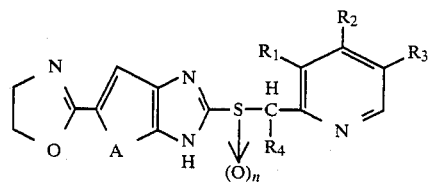

in which
A is —CH=CH— or —S—,
$R_1$, $R_3$ and $R_4$, independently of one another, is hydrogen or lower alkyl,
$R_2$ is hydrogen or lower alkoxy, and
n is 0 or 1.

2. A compound of the formula I defined in claim 1, in which n is the number 1.

3. A compound of the formula I as claimed in claim 1 in which $R_1$, $R_3$ and $R_4$ is hydrogen or methyl.

4. A compound of the formula I as claimed in claim 1, in which $R_2$ is hydrogen or methoxy.

5. A pharmaceutical composition having a compound of formula I as claimed in claim 1 in an amount effective for the treatment and prophylaxis of disorders which are caused by increased gastric secretions, in combination with pharmaceutically acceptable excipients, carrier or diluents.

6. A method for the treatment of prophylaxis of diseases, caused by increased gastric secretions, which comprises administering an effective amount of a compound of formula I as claimed in claim 1 to a patient, suffering from increased gastric secretions.

* * * * *